United States Patent
Johns et al.

(10) Patent No.: US 10,118,894 B2
(45) Date of Patent: Nov. 6, 2018

(54) ISOINDOLINONE DERIVATIVES USEFUL AS ANTIVIRAL AGENTS

(71) Applicant: VIIV HEALTHCARE UK LIMITED, Brentford, Middlesex (GB)

(72) Inventors: Brian Alvin Johns, Research Triangle Park, NC (US); Emile Johann Velthuisen, Research Triangle Park, NC (US); Jason Gordon Weatherhead, Research Triangle Park, NC (US)

(73) Assignee: ViiV HEALTHCARE UK LIMITED, Brentford, Middlesex (GB)

( * ) Notice: Subject to any disclaimer, the term of this patent is extended or adjusted under 35 U.S.C. 154(b) by 0 days.

(21) Appl. No.: 15/326,100

(22) PCT Filed: Jul. 20, 2015

(86) PCT No.: PCT/IB2015/055489
§ 371 (c)(1),
(2) Date: Jan. 13, 2017

(87) PCT Pub. No.: WO2016/012930
PCT Pub. Date: Jan. 28, 2016

(65) Prior Publication Data
US 2017/0204058 A1    Jul. 20, 2017

Related U.S. Application Data

(60) Provisional application No. 62/027,359, filed on Jul. 22, 2014.

(51) Int. Cl.
| | |
|---|---|
| C07D 209/46 | (2006.01) |
| C07D 413/04 | (2006.01) |
| C07D 401/04 | (2006.01) |
| C07D 405/04 | (2006.01) |

(52) U.S. Cl.
CPC ......... *C07D 209/46* (2013.01); *C07D 401/04* (2013.01); *C07D 405/04* (2013.01); *C07D 413/04* (2013.01)

(58) Field of Classification Search
None
See application file for complete search history.

(56) References Cited

FOREIGN PATENT DOCUMENTS

| WO | WO 2009/026248 A2 | 2/2009 |
|---|---|---|
| WO | WO 2013/016441 A1 | 1/2013 |

OTHER PUBLICATIONS

Chemical Abstract Registry No. 1260845-50-8, indexed in the Registry File on STN CAS Online Jan. 27, 2011.*
Jonas Demeulemeester, et al. Expert Opinion on Therapeutic Patents, 24 (6): 609-632 (Jun. 1, 2014), (International search report only).

* cited by examiner

*Primary Examiner* — Po-Chih Chen
(74) *Attorney, Agent, or Firm* — Robert H. Brink; Edward R. Gimmi; William R. Majarian

(57) ABSTRACT

Compounds of Formula I are disclosed and methods of treating viral infections with compositions comprising such compounds.

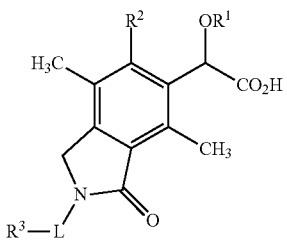

Formula I

9 Claims, No Drawings

ISOINDOLINONE DERIVATIVES USEFUL AS ANTIVIRAL AGENTS

This application is a § 371 of International Application No. PCT/IB2015/055489, filed 20 Jul. 2015, which claims the benefit of U.S. Provisional Application No. 62/027,359, filed 22 Jul. 2014.

FIELD OF THE INVENTION

The present invention relates to substituted isoindolinone compounds, pharmaceutical compositions, and methods of use thereof for (i) inhibiting HIV replication in a subject infected with HIV, or (ii) treating a subject infected with HIV, by administering such compounds.

FIELD OF THE INVENTION

The present invention relates to substituted isoindoline compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

Briefly, in one aspect, the present invention discloses compounds of Formula I:

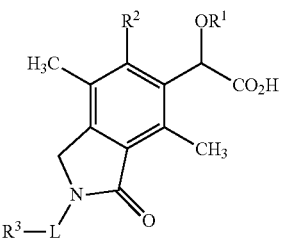

Formula I wherein:

$R^1$ is $C_{1-6}$alkyl;

$R^2$ is $C_{5-14}$aryl, $C_{3-7}$cycloalkyl, $(C_{3-7})$cycloalkenyl, $(C_{2-9})$heterocycle, and $(C_{2-9})$heteroaryl, each of which is optionally substituted by one to four substituents selected from halo, $C_{1-6}$alkyl, $C_{1-6}$hetereoalkyl, or $C_{1-6}$alkylene or $C_{1-6}$hetereoalklylene wherein said $C_{1-6}$alkylene or $C_{1-6}$hetereoalklylene are bonded to adjacent carbon atoms on said of $C_{5-14}$aryl, $C_{3-7}$cycloalkyl, $(C_3-C_7)$cycloalkenyl, $(C_2-C_9)$heterocycle or $(C_2-C_9)$heteroaryl to form a ring, and wherein each heterocycle, heteroaryl, heteroalkyl, and hetereoalkylene comprises one to three heteroatoms selected from S, N or O;

L is a bond or $C_{1-3}$alkylene:

$R^3$ is H, $C_{1-6}$alkyl, $C_{5-14}$aryl, $C_{3-7}$cycloalkyl, $(C_{3-7})$cycloalkenyl, $(C_{2-9})$heterocycle, and $(C_{2-9})$heteroaryl, each of which is optionally substituted by one to four substituents selected from halo, $C_{1-6}$alkyl, and wherein each heterocycle and heteroaryl comprises one to three heteroatoms selected from S, N or O;

In another aspect the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

DETAILED DESCRIPTION OF THE INVENTION

Preferably $R^1$ is t-butyl.

Preferably $R^2$ is optionally substituted phenyl or cyclohexenyl. Most preferably, $R^2$ is phenyl optionally substituted by one to four substituents selected from fluorine, methyl, or —$CH_2CH_2CH_2O$— or —$NHCH_2CH_2O$— wherein said —$CH_2CH_2CH_2O$— or —$NHCH_2CH_2O$— is bonded to adjacent carbon atoms on said phenyl to form a bicyclic ring.

Preferably $R^3$ is phenyl.

Preferably the stereochemistry on the carbon to which $OR^1$ is bound is as depicted below.

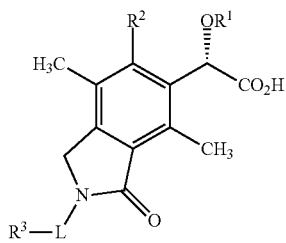

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The method of treating or preventing metabolic disorders may comprise administration of a compound or salt of this invention alone as mono-therapy. The compounds and salts of this invention may also be used in combination with other therapeutic agents. Suitable agents for use in combination with the compounds and salts of this invention include, for example, insulin sensitivity enhancers, glucose absorption inhibitors, biquanides, insulin secretion enhancers, or metformin.

EXAMPLES

The compounds of this invention may be made by a variety of methods, including well-known standard synthetic methods. Illustrative general synthetic methods are set out below and then specific compounds of the invention are prepared in the working examples.

Scheme 1

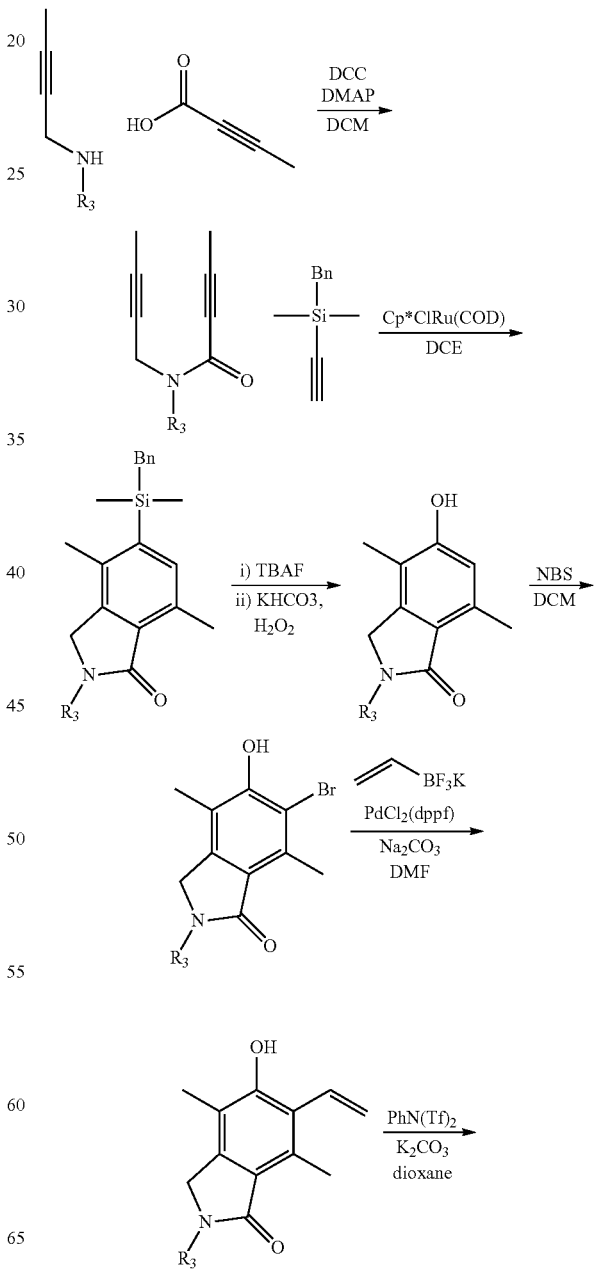

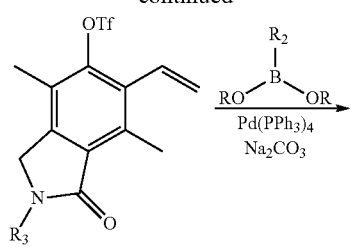

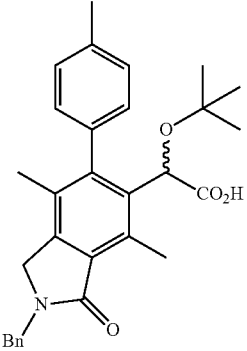 [SMILES: Cc1ccc(-c2c(C)c3c(c(C)c2C(OC(C)(C)C)C(=O)O)C(=O)N(Cc2ccccc2)C3)cc1]

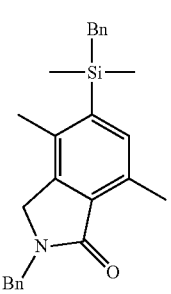

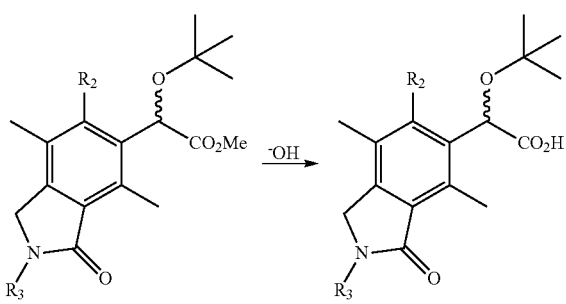

Example 1: 2-(2-Benzyl-4,7-dimethyl-3-oxo-6-(p-tolyl)isoindolin-5-yl)-2-(tert-butoxy)acetic acid Step 1: 2-Benzyl-5-(benzyldimethylsilyl)-4,7-dimethylisoindolin-1-one N-Benzyl-N-(but-2-yn-1-yl)but-2-ynamide was prepared from the known procedure as described in *Org. Biomol. Chem.*, 2004, 2, 1287-1294.

Benzyl(ethynyl)dimethylsilane was prepared from the known procedure as described in *J. Am. Chem. Soc.*, 2005, 127, 3666-36667.

A solution of benzyl(ethynyl)dimethylsilane (5.2 g, 29.8 mmol) in 1,2-DCE (15 mL) was degassed with $N_2$ for 5 min and treated with Cp*ClRu(cod) (0.253 g, 0.666 mmol). To this was added degassed solution of N-benzyl-N-(but-2-yn-1-yl)but-2-ynamide (1.5 g, 6.66 mmol) in 1,2-DCE (15 mL) dropwise over 10 min. After 1 h, the reaction mixture was concentrated in vacuo and the residue purified by silica gel chromatography (0-30% EtOAc/hexanes) to afford the title compound as a yellow solid (1.66 g 62% yield; 4:1 mixture of regioisomers). Major isomer—$^1$H NMR (400 MHz, CHLOROFORM-d) δ=7.39-7.29 (m, 5H), 7.26 (s, 1H), 7.22-7.15 (m, 2H), 7.11-7.05 (m, 1H), 7.00-6.91 (m, 2H), 4.81 (s, 2H), 4.16-4.09 (m, 2H), 2.99-2.66 (m, 3H), 2.46-2.36 (m, 2H), 2.28-2.18 (m, 3H), 0.37-0.29 (m, 6H); LC/MS (m/z) ES$^+$=400 (M+1)

Step 2: 2-benzyl-5-hydroxy-4,7-dimethylisoindolin-1-one

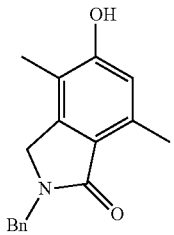

An ice cold solution of 2-benzyl-5-(benzyldimethylsilyl)-4,7-dimethylisoindolin-1-one (1.66 g, 4.15 mmol) in Tetrahydrofuran (10 mL) was treated with TBAF (16.62 mL, 16.62 mmol) dropwise over a 5 min period. After 10 additional min, methanol (30 mL), KHCO$_3$ (0.832 g, 8.31 mmol) and H$_2$O$_2$ (4.24 mL, 41.5 mmol) were added and the mixture was warmed to ambient temperature. After 45 min, the reaction mixture was partitioned between sat. aq. Na$_2$S$_2$O$_3$ (1 mL) and EtOAc (3×10 mL). The organic layer was washed with brine, dried (MgSO$_4$), filtered and concentrated in vacuo. The residue was purified by silica gel chromatography (0-3% MeOH/DCM) to afford the title compound (0.67 g, 60%) as a white solid. $^1$H NMR (400 MHz, CHLOROFORM-d) δ=7.37-7.28 (m, 6H), 6.67 (s, 1H), 5.82 (br. s., 1H), 4.77 (s, 2H), 4.10 (s, 2H), 2.66 (s, 3H), 2.08 (s, 3H); LC/MS (m/z) ES+=268 (M+1)

Step 3: 2-benzyl-6-bromo-5-hydroxy-4,7-dimethyl-isoindolin-1-one

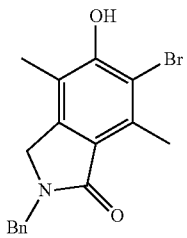

A suspension of 2-benzyl-5-hydroxy-4,7-dimethylisoindolin-1-one (1.6 g, 6.0 mmol) and NaHCO$_3$ (1.5 g, 18.0 mmol) in DCM (30 mL) was treated with NBS (1.6 g, 9.0 mmol). After 20 min, the reaction mixture was treated with saturated aqueous Na$_2$S$_2$O$_3$ and the layers partitioned. The organic phase was washed with water, dried (Na$_2$SO$_4$), filtered and concentrated in vacuo. The residue was purified by silica gel chromatography (0-100% EtOAc-hexanes) to afford the title compound as a white solid (1.5 g, 70% yield). $^1$H NMR (400 MHz, CHLOROFORM-d) δ=7.29 (m, 5H), 6.01 (s, 1H), 4.75 (s, 2H), 4.05 (s, 2H), 2.81 (s, 3H), 2.15 (s, 3H); LC/MS (m/z) ES+=348 (M+2).

Step 4: 2-benzyl-5-hydroxy-4,7-dimethyl-6-vinylisoindolin-1-one

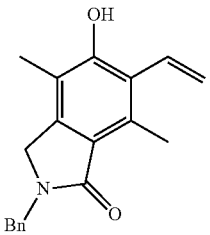 [SMILES: C=Cc1c(C)c2c(c(C)c1O)CN(Cc1ccccc1)C2=O]

A solution of 2-benzyl-6-bromo-5-hydroxy-4,7-dimethylisoindolin-1-one (300 mg, 0.867 mmol), potassium vinyltrifluoroborate (464 mg, 3.468 mmol) and Na$_2$CO$_3$ (8.67 mL, 4.335 mmol, 2 M aqueous) in 1,4-dioxane (12 mL) was degassed with N$_2$ for 5 min and treated with Pd(dppf)Cl$_2$.DCM (142 mg, 0.1734 mmol) and heated to 100° C. After 3 h, the reaction mixture was cooled to ambient temperature and filtered through a pad of Celite and the solids washed with EtOAc. The filtrate was concentrated in vacuo and the residue purified by silica gel chromatography (0-100% EtOAc-hexanes) to afford the title compound (150 mg, 60% yield) as a colorless oil. $^1$H NMR (400 MHz, CHLOROFORM-d) δ=7.31 (m, 5H), 6.74 (m, 1H), 6.02 (s, 1H), 5.81 (dd, 1H), 5.55 (dd, 1H), 4.77 (s, 2H), 4.09 (s, 2H), 2.67 (s, 3H), 2.11 (s, 3H); LC/MS (m/z) ES+=294 (M+H).

Step 5: 2-benzyl-4,7-dimethyl-1-oxo-6-vinylisoindolin-5-yl trifluoromethanesulfonate

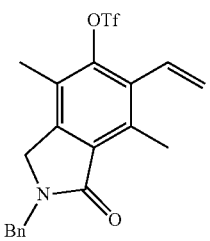 [SMILES: C=Cc1c(C)c2c(c(C)c1OS(=O)(=O)C(F)(F)F)CN(Cc1ccccc1)C2=O]

A suspension of 2-benzyl-5-hydroxy-4,7-dimethyl-6-vinylisoindolin-1-one (150 mg, 0.614 mmol) and K$_2$CO$_3$ (85 mg, 0.614 mmol) in DMF (4 mL) was treated with 1,1,1-trifluoro-N-phenyl-N-((trifluoromethyl)sulfonyl)methanesulfonamide (219 mg, 0.614 mmol). After 1 h, the reaction mixture was diluted with EtOAc and poured into water. The layers were partitioned and the organic phase washed with brine, dried (MgSO$_4$), and concentrated in vacuo. The residue was purified by silica gel chromatography (0-100% EtOAc-hexanes) to afford the title compound (191 mg, 88% yield) as a colorless oil. $^1$H NMR (400 MHz, CHLOROFORM-d) δ 7.32 (m, 5H), 6.66 (m, 1H), 5.73 (dd, 1H), 5.45 (d, 1H), 4.78 (s, 2H), 4.13 (s, 2H), 2.74 (s, 3H), 2.25 (s, 3H); LC/MS (m/z) ES+=426 (M+H).

Step 6: 2-benzyl-4,7-dimethyl-5-(p-tolyl)-6-vinylisoindolin-1-one

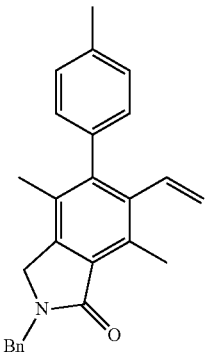 [SMILES: C=Cc1c(C)c2c(c(C)c1-c1ccc(C)cc1)CN(Cc1ccccc1)C2=O]

A solution of 2-benzyl-4,7-dimethyl-1-oxo-6-vinylisoindolin-5-yl trifluoromethanesulfonate (175 mg, 0.412 mmol), p-tolylboronic acid (224 mg, 1.648 mmol), and $Na_2CO_3$ (4 mL, 2.06 mmol, 2.0 M aqueous) in DMF (5 mL) was degassed with N2 for 5 min, treated with tetrakis(triphenylphosphine)palladium(0) (95 mg, 0.0824 mmol) and heated to 80° C. After 30 min, the reaction mixture was cooled to ambient temperature, diluted with EtOAc and filtered through a pad of Celite. The solids were washed with EtOAc and the filtrate was washed with water, brine, dried (MgSO4), filtered, and concentrated in vacuo. The residue was purified by silica gel chromatography (0-100% EtOAc-hexanes) to afford the title compound (114 mg, 75% yield) as a colorless oil. $^1$H NMR (400 MHz, CHLOROFORM-d) δ 7.31 (m, 5H), 7.18 (d, 2H), 6.94 (d, 2H), 6.32 (m, 1H), 5.30 (m, 1H), 5.04 (m, 1H), 4.81 (s, 2H), 4.12 (s, 2H), 2.80 (s, 3H), 2.38 (s, 3H), 1.88 (s, 3H); LC/MS (m/z) ES+=368 (M+H).

Steps 7: 2-benzyl-4,7-dimethyl-3-oxo-6-(p-tolyl)isoindoline-5-carbaldehyde

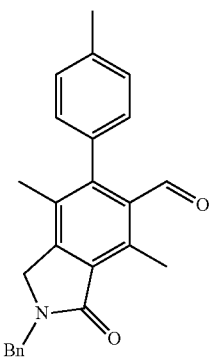

A solution of 2-benzyl-4,7-dimethyl-5-(p-tolyl)-6-vinylisoindolin-1-one (110 mg, 0.299 mmol) in THF/H$_2$O (6 mL of a 3:1 solution) was treated with potassium osmate dihydrate (44.1 mg, 0.120 mmol) and sodium periodate (384 mg, 1.796 mmol). After 30 min, the reaction mixture was treated with Na$_2$S$_2$O$_3$ (6 mL, 10% aqueous solution) and extracted with EtOAc. The organic layer was washed with water, brine, dried (MgSO4), filtered and concentrated in vacuo. The residue was purified by silica gel chromatography (0-100% EtOAc-hexanes) to afford the title compound (42 mg, 38%) as a white solid. $^1$H NMR (400 MHz, CHLOROFORM-d) δ 9.79 (s, 1H), 7.33 (m, 5H), 7.26 (d, 2H), 7.05 (d, 2H), 4.82 (s, 2H), 4.18 (s, 2H), 3.06 (s, 3H), 2.42 (s, 3H), 1.96 (s, 3H); LC/MS (m/z) ES+=370 (M+H).

Steps 8, 9, 10: Methyl 2-(2-benzyl-4,7-dimethyl-3-oxo-6-(p-tolyl)isoindolin-5-yl)-2-(tert-butoxy)acetate

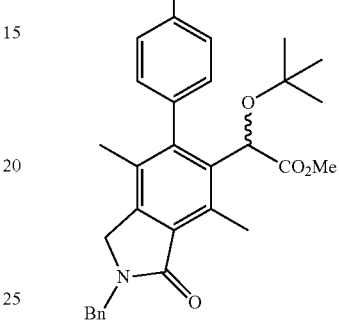

An ice cold solution of 2-benzyl-4,7-dimethyl-3-oxo-6-(p-tolyl)isoindoline-5-carbaldehyde (42 mg, 0.114 mmol) in DCM (3 mL) was treated with zinc(II) iodide (18 mg, 0.057 mmol, 0.5 equiv) and trimethylsilanecarbonitrile (0.153 mL, 1.14 mmol, 10 equiv). After 10 min, the reaction mixture was treated with water and the layers partitioned. The organic layer was washed with brine, dried (Na$_2$SO$_4$), filtered and concentrated in vacuo to afford 2-(2-benzyl-4,7-dimethyl-3-oxo-6-(p-tolyl)isoindolin-5-yl)-2-((trimethylsilyl)oxy)acetonitrile (60 mg crude) that was used immediately without further purification. LC/MS (m/z) ES+=469 (M+H).

An ice cold solution of 2-(2-benzyl-4,7-dimethyl-3-oxo-6-(p-tolyl)isoindolin-5-yl)-2-((trimethylsilyl)oxy)acetonitrile (60 mg, 0.129 mmol) in MeOH (40 mL) was bubbled with HCl (g). After 30 min, the reaction mixture was concentrated in vacuo and treated with HCl (aq.) (100 mL, 1.0 N) and heated to 90° C. After 1 h, the reaction mixture was cooled to ambient temperature and extracted with EtOAc. The organic phase was then washed with brine, dried (MgSO4), filtered and concentrated in vacuo to afford methyl 2-(2-benzyl-4,7-dimethyl-3-oxo-6-(p-tolyl)isoindolin-5-yl)-2-hydroxyacetate (70 mg crude) that was used immediately without further purification. LC/MS (m/z) ES+=430 (M+H).

A solution of 2-(2-benzyl-4,7-dimethyl-3-oxo-6-(p-tolyl)isoindolin-5-yl)-2-hydroxyacetate (70 mg, 0.163 mmol) in tert-butyl acetate (15 mL) was treated with HClO$_4$ (0.49 mL, 70%). After 15 min, the reaction mixture was cooled to 0° C. and the pH adjusted to 8 using aqueous 50% NaOH. The aqueous layer was extracted with EtOAc, and the organic layer dried (MgSO$_4$), filtered and concentrated in vacuo. The residue was purified by silica gel chromatography (0-100% EtOAc-hexanes) to afford the title compound (24 mg, 43% over three steps) as a colorless oil. $^1$H NMR (400 MHz, CHLOROFORM-d) δ 7.32 (m, 5H), 7.23 (m, 3H), 7.04 (d, 1H), 5.07 (s, 1H), 4.78 (s, 2H), 4.09 (s, 2H), 3.67 (s, 3H), 2.85 (s, 3H), 2.40 (s, 3H), 1.83 (s, 3H), 0.94 (s, 9H); LC/MS (m/z) ES+=486 (M+H).

Step 11: (2-(2-Benzyl-4,7-dimethyl-3-oxo-6-(p-tolyl)isoindolin-5-yl)-2-(tert-butoxy)acetic acid

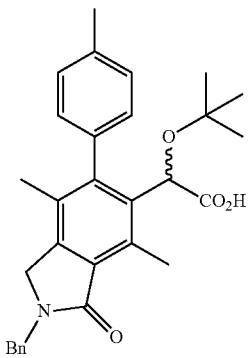

A solution of Methyl 2-(2-benzyl-4,7-dimethyl-3-oxo-6-(p-tolyl)isoindolin-5-yl)-2-(tert-butoxy)acetate (10 mg, 0.021 mmol) in 1,4-dioxane (2 mL) was treated with LiOH (0.52 mL, 0.52 mmol, 1.0 M aqueous) and heated to 80° C. After 6 h, the reaction mixture was concentrated in vacuo, and partitioned between EtOAc and 1M HCl. The organic phase was washed with brine, dried (MgSO$_4$), filtered and concentrated in vacuo. The residue was purified by reverse phase HPLC to afford the title compound (6 mg, 62%) as a white solid. $^1$H NMR (400 MHz, CHLOROFORM-d) δ 7.30 (m, 8H), 7.05 (d, 1H), 5.20 (s, 1H), 4.79 (d, 2H), 4.10 (d, 2H), 2.84 (s, 3H), 2.40 (s, 3H), 1.85 (s, 3H), 0.97 (s, 9H); LC/MS (m/z) ES+=472 (M+H).

Example 2: (S)-(2-(2-Benzyl-4,7-dimethyl-3-oxo-6-(p-tolyl)isoindolin-5-yl)-2-(tert-butoxy)acetic acid

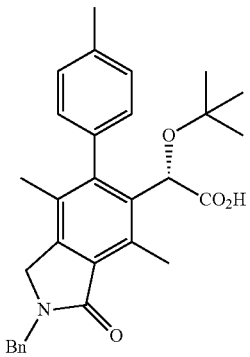

A sample of 2-(2-Benzyl-4,7-dimethyl-3-oxo-6-(p-tolyl) isoindolin-5-yl)-2-(tert-butoxy)acetic acid was purified using an S,S Whelk-O column (250×30 mm i.d., 5 μm; Regis Technologies, Morton Grove, Ill.) under supercritical conditions maintained at 40° C., 140 bar, with methanol modified CO$_2$ (30% MeOH, 70% CO$_2$) delivered at a combined flow rate of 90 ml/min on a PIC prep SFC system (PIC Solution; Avignon, France). Triggered collections were made using a Knauer selectable wavelength UV-Vis dectector at 220 nm.
Chiral purity was determined by chiral analytical HPLC on a S,S Whelk-O column (250×4.6 mm i.d., 5 μm; RegisTechnologies, Morton Grove, Ill.) under supercritical conditions maintained at 40° C., 140 bar, with methanol modified CO$_2$ (40% MeOH, 60% CO$_2$) delivered at a combined flow rate of 2 ml/min on an Aurora Fusion A5 Evolution SFC system (Agilent Technologies, Santa Clara, Calif.) equipped with a DAD detector and monitored at 220 nm. Retention time of the title compound under these conditions was 5.67 min.

Example 3: 2-(2-benzyl-6-(4-chlorophenyl)-4,7-dimethyl-3-oxoisoindolin-5-yl)-2-(tert-butoxy)acetic acid

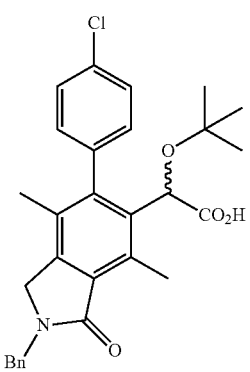 [SMILES: Cc1c2c(c(C)c(C(OC(C)(C)C)C(=O)O)c1-c1ccc(Cl)cc1)C(=O)N(Cc1ccccc1)C2]

The title compound was made in a similar manner as Example 1 except using 4-chlorophenylboronic acid in Step 5. $^1$H NMR (400 MHz, CHLOROFORM-d) δ=7.54-7.30 (m, 8H), 7.12 (br. s., 1H), 5.21-5.06 (m, 1H), 4.81 (s, 2H), 4.13 (d, J=2.0 Hz, 2H), 2.87 (br. s., 3H), 1.86 (s, 3H), 1.11-0.98 (m, 9H); LC/MS (m/z) ES$^+$=492 (M+1).

Example 4: 2-(2-benzyl-6-(chroman-6-yl)-4,7-dimethyl-3-oxoisoindolin-5-yl)-2-(tert-butoxy)acetic acid

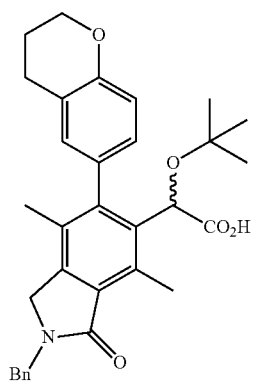 [SMILES: Cc1c2c(c(C)c(C(OC(C)(C)C)C(=O)O)c1-c1ccc3c(c1)CCCO3)C(=O)N(Cc1ccccc1)C2]

The title compound was made in a similar manner as Example 1 except using 2-(chroman-6-yl)-4,4,5,5-tetramethyl-1,3,2-dioxaborolane in Step 5. $^1$H NMR (400 MHz, CHLOROFORM-d) δ=7.39-7.29 (m, 5H), 7.17 (br. s., 1H), 6.92-6.77 (m, 2H), 5.27 (br. s., 1H), 4.89-4.75 (m, 2H), 4.24 (t, J=5.1 Hz, 2H), 4.12 (br. s., 2H), 2.91-2.75 (m, 5H), 2.11-2.00 (m, 2H), 1.90 (d, J=4.5 Hz, 3H), 1.01 (br. s., 9H); LC/MS (m/z) ES$^+$=514 (M+1).

Scheme 2
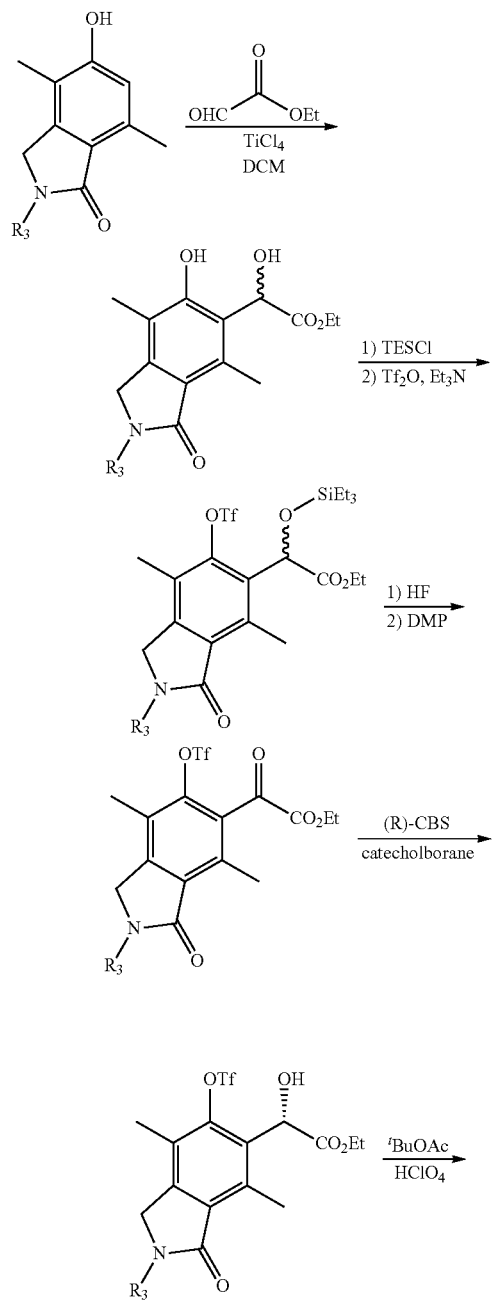
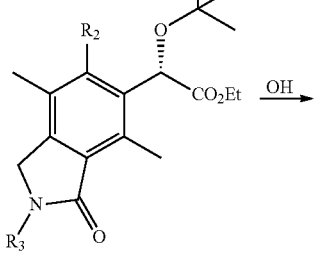
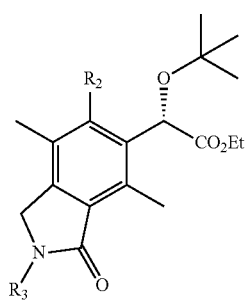
Example 5: (S)-2-((M)-2-Benzyl-6-(8-fluoro-5-methylchroman-6-yl)-4,7-dimethyl-3-oxoisoindolin-5-yl)-2-(tert-butoxy)acetic acid
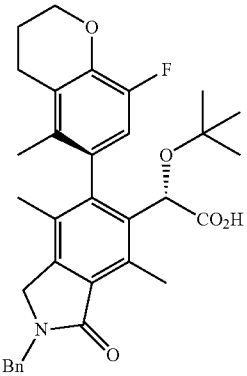
Step 1: Ethyl 2-(2-benzyl-6-hydroxy-4,7-dimethyl-3-oxoisoindolin-5-yl)-2-hydroxyacetate
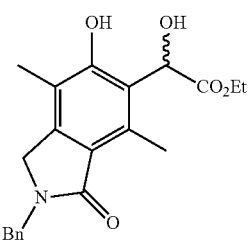 [SMILES: CCOC(=O)C(O)c1c(C)c2c(c(C)c1O)CN(Cc1ccccc1)C2=O]
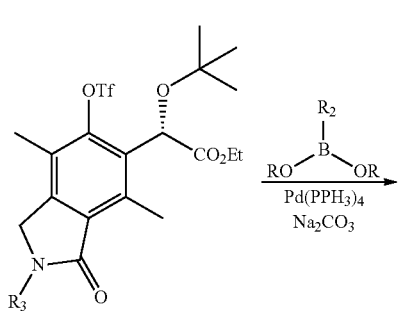
2-(8-fluoro-5-methylchroman-6-yl)-4,4,5,5-tetramethyl-1,3,2-dioxaborolane was prepared from the known procedure described in WO2009/062285.

An ice cold solution of 2-benzyl-5-hydroxy-4,7-dimethylisoindolin-1-one (1 g, 3.74 mmol) in DCM (30 mL) was treated with TiCl$_4$ (0.413 mL, 3.74 mmol). After 5 min, ethyl 2-oxoacetate (0.742 mL, 3.74 mmol) was added. After 5 h, the reaction mixture was cooled to 0° C. and treated with additional TiCl$_4$ (0.207 mL, 1.87 mmol). After 18 h, the reaction mixture was poured into water and extracted with EtOAc. The organic layer was washed with brine, dried (Na$_2$SO$_4$), filtered and concentrated in vacuo. The residue was purified by silica gel chromatography (0-100% EtOAc-hexanes) to afford the title compound (1.01 g, 73% yield) as a white foam. $^1$H NMR (400 MHz, CHLOROFORM-d) =8.22 (s, 1H), 7.38-7.28 (m, 5H), 5.73 (s, 1H), 4.85-4.67 (m, 2H), 4.30 (qd, J=7.1, 10.7 Hz, 1H), 4.18-4.11 (m, 1H), 4.05 (s, 2H), 3.84 (s, 1H), 2.84 (s, 3H), 2.08-2.04 (m, 3H), 1.22 (t, J=7.2 Hz, 3H); LC/MS (m/z) ES+=370 (M+1).

Step 2: Ethyl 2-(2-benzyl-4,7-dimethyl-3-oxo-6-(((trifluoromethyl)sulfonyl)oxy)isoindolin-5-yl)-2-((triethylsilyl)oxy)acetate

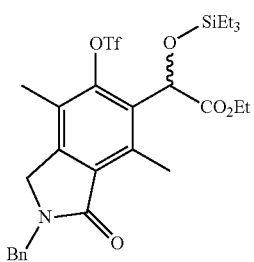

An ice cold solution of ethyl 2-(2-benzyl-6-hydroxy-4,7-dimethyl-3-oxoisoindolin-5-yl)-2-hydroxyacetate (1 g, 2.71 mmol) in dichloromethane (20 mL) was treated with imidazole (0.332 g, 4.87 mmol) and chlorotriethylsilane (0.545 mL, 3.25 mmol). After 30 min, the reaction mixture was poured into water and the layers partitioned. The organic layer was washed with 1N HCl, brine, dried (Na$_2$SO$_4$), filtered and concentrated in vacuo to afford methyl 2-(2-benzyl-6-hydroxy-4,7-dimethyl-3-oxoisoindolin-5-yl)-2-((triethylsilyl)oxy)acetate as a yellow oil. $^1$H NMR (400 MHz, CHLOROFORM-d) δ=8.72 (s, 1H), 7.37-7.28 (m, 5H), 5.68 (s, 1H), 4.76 (d, J=2.0 Hz, 2H), 4.27-4.17 (m, 1H), 4.15-4.08 (m, 1H), 4.06 (d, J=2.0 Hz, 2H), 2.85 (s, 3H), 2.06 (s, 3H), 1.03-0.90 (m, 15H); LC/MS (m/z) ES+=484 (M+1).

The residue was dissolved in DCM (30 mL), cooled to −78° C. and treated with triethylamine (0.874 mL, 6.27 mmol) and Tf$_2$O (0.457 mL, 2.71 mmol). After 1 h, the reaction mixture was poured into water and the layers partitioned. The organic layer was washed with 1 N HCl, sat. aq. NaHCO$_3$, dried (Na$_2$SO$_4$), filtered and concentrated in vacuo. The residue was purified by silica gel chromatography (0-100% EtOAc-hexanes) to afford the title compound (1.48 g, 89% yield) as a colorless gum. $^1$H NMR (400 MHz, CHLOROFORM-d) δ=7.41-7.29 (m, 5H), 5.74 (s, 1H), 4.89-4.68 (m, 2H), 4.30-4.07 (m, 4H), 2.81 (s, 3H), 2.26 (s, 3H), 1.20 (t, J=7.2 Hz, 3H), 0.93-0.86 (m, 9H), 0.69-0.54 (m, 6H); LC/MS (m/z) ES+=616 (M+1).

Step 3: Ethyl 2-(2-benzyl-4,7-dimethyl-3-oxo-6-(((trifluoromethyl)sulfonyl)oxy)isoindolin-5-yl)-2-oxoacetate

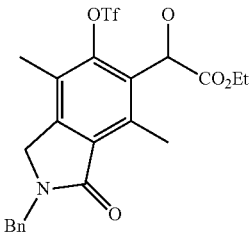 [SMILES: CCOC(=O)C(O)c1c(C)c2c(c(C)c1OS(=O)(=O)C(F)(F)F)CN(Cc1ccccc1)C2=O]

An ice cold solution of ethyl 2-(2-benzyl-4,7-dimethyl-3-oxo-6-(((trifluoromethyl)sulfonyl)oxy)isoindolin-5-yl)-2-((triethylsilyl)oxy)acetate (1.46 g, 2.371 mmol) in tetrahydrofuran (20 mL) was treated with 48% HF (5.0 mL, 138 mmol) and warmed to ambient temperature. After 1.5 h, the reaction mixture was diluted with EtOAc and quenched with the addition of solid NaHCO$_3$. The reaction mixture was filtered through a pad of Celite and the filtrated was extracted with EtOAc. The combined organic extracts were washed with brine, dried (Na$_2$SO$_4$), filtered and concentrated in vacuo to afford ethyl 2-(2-benzyl-4,7-dimethyl-3-oxo-6-(((trifluoromethyl)sulfonyl)oxy)isoindolin-5-yl)-2-hydroxyacetate (1.1 g, 97%) as a white foam. 1H NMR (400 MHz, CHLOROFORM-d)=7.40-7.29 (m, 5H), 5.64 (d, J=2.5 Hz, 1H), 4.79 (d, J=3.0 Hz, 2H), 4.37-4.20 (m, 2H), 4.16 (s, 2H), 3.42 (d, J=2.8 Hz, 1H), 2.78 (s, 3H), 2.27 (s, 3H), 1.23 (t, J=7.2 Hz, 3H); LC/MS (m/z) ES+=502 (M+1).

A solution of ethyl 2-(2-benzyl-4,7-dimethyl-3-oxo-6-(((trifluoromethyl)sulfonyl)oxy)isoindolin-5-yl)-2-hydroxyacetate (1.1 g, 2.293 mmol) in DCM (20 mL) was treated with Dess-Martin periodinane (1.207 g, 2.85 mmol). After 1 h, the reaction mixture was quenched with the addition of sat. aq. Na$_2$S$_2$O$_3$ and sat. aq. NaHCO$_3$. After 15 min, the reaction mixture was diluted with DCM and the layers partitioned. The combined organic extracts were dried (Na$_2$SO$_4$), filtered and concentrated in vacuo to afford the title compound (1.1 g, 93%) as a yellow foam. $^1$H NMR (400 MHz, CHLOROFORM-d) δ=7.41-7.29 (m, 5H), 4.81 (s, 2H), 4.40 (q, J=7.1 Hz, 2H), 4.21 (s, 2H), 2.74 (s, 3H), 2.33-2.28 (m, 3H), 1.39 (t, J=7.2 Hz, 3H); LC/MS (m/z) ES+=500 (M+1).

Step 5: (S)-Ethyl 2-(2-benzyl-4,7-dimethyl-3-oxo-6-(((trifluoromethyl)sulfonyl)oxy)isoindolin-5-yl)-2-hydroxyacetate

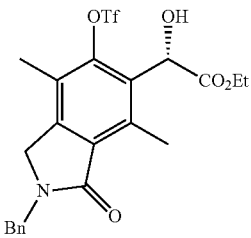 [SMILES: CCOC(=O)[C@@H](O)c1c(C)c2c(c(C)c1OS(=O)(=O)C(F)(F)F)CN(Cc1ccccc1)C2=O]

A −45° C. solution of ethyl 2-(2-benzyl-4,7-dimethyl-3-oxo-6-(((trifluoromethyl)sulfonyl)oxy)isoindolin-5-yl)-2- oxoacetate (1.1 g, 2.102 mmol) and (R)-CBS (117 mg, 0.420 mmol) in toluene (15 mL) was treated dropwise with catecholborane (4.20 mL, 4.20 mmol, 1.0 M in THF). The reaction mixture was allowed to warm to −20° C. over 1.5 h. The reaction mixture was diluted with EtOAc and treated with 2M aqueous Na₂CO₃. The reaction mixture was stirred vigorously for 30 min and the layers partitioned. The organic layer was washed with sat. aq. NH₄Cl, dried (Na₂SO₄), filtered and concentrated in vacuo. The residue was purified by silica gel chromatography (0-100% EtOAc-hexanes) to afford the title compound (950 mg, 90% yield) as a gummy solid. 1H NMR (400 MHz, CHLOROFORM-d) δ=7.40-7.29 (m, 5H), 5.64 (d, J=2.5 Hz, 1H), 4.79 (d, J=1.8 Hz, 2H), 4.37-4.21 (m, 2H), 4.16 (s, 2H), 3.42 (d, J=2.8 Hz, 1H), 2.79 (s, 3H), 2.28 (s, 3H), 1.24 (t, J=7.0 Hz, 3H); LC/MS (m/z) ES+=502 (M+1).

Step 6: (S)-Ethyl 2-(2-benzyl-4,7-dimethyl-3-oxo-6-(((trifluoromethyl)sulfonyl)oxy)isoindolin-5-yl)-2-(tert-butoxy)acetate

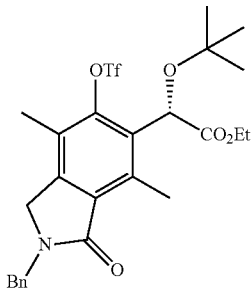 [SMILES: CCOC(=O)[C@@H](OC(C)(C)C)c1c(C)c2c(c(C)c1OS(=O)(=O)C(F)(F)F)CN(Cc1ccccc1)C2=O]

Step 7: (S)-Ethyl 2-((M)-2-benzyl-6-(8-fluoro-5-methylchroman-6-yl)-4,7-dimethyl-3-oxoisoindolin-5-yl)-2-(tert-butoxy)acetate

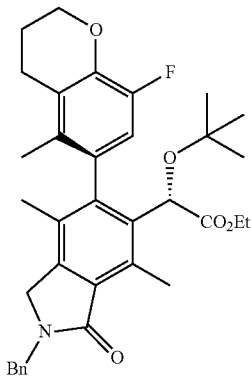

A solution of (S)-Methyl 2-(2-benzyl-4,7-dimethyl-3-oxo-6-(((trifluoromethyl)sulfonyl)oxy)isoindolin-5-yl)-2-(tert-butoxy)acetate (120 mg, 0.215 mmol), 2-(8-fluoro-5-methylchroman-6-yl)-4,4,5,5-tetramethyl-1,3,2-dioxaborolane (81.73 mg, 0.279 mmol), and cesium fluoride (130.7 mg, 0.86 mmol) in DME (5 mL) was degassed with N₂ for 5 min, treated with Sphos palladacycle (49.11 mg, 0.065 mmol) and irradiated in the microwave for 40 min at 130° C. The reaction mixture was diluted with EtOAc, washed with sat. aq. NaHCO3, brine, dried (Na2SO4), filtered and concentrated in vacuo. The residue was purified using silica gel chromatography (0-50% EtOAc-hexanes) to afford the title compound (30 mg, 24%) as a white solid. ¹H NMR (400 MHz, CHLOROFORM-d) δ=7.37-7.28 (m, 5H), 6.62 (d, J=11.3 Hz, 1H), 5.04 (s, 1H), 4.80 (s, 2H), 4.28 (t, J=5.1 Hz, 2H), 4.13-4.04 (m, 4H), 2.93 (s, 3H), 2.70 (d, J=4.8 Hz, 2H), 2.14 (d, J=5.3 Hz, 2H), 1.79 (s, 3H), 1.75 (s, 3H), 1.17 (t, J=7.2 Hz, 3H), 1.10 (s, 9H); LC/MS (m/z) ES+=574 (M+1).

Step 8: (S)-2-((M)-2-benzyl-6-(8-fluoro-5-methylchroman-6-yl)-4,7-dimethyl-3-oxoisoindolin-5-yl)-2-(tert-butoxy)acetic acid

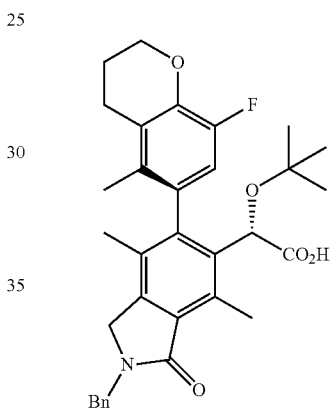

A solution of (S)-ethyl 2-((M)-2-benzyl-6-(8-fluoro-5-methylchroman-6-yl)-4,7-dimethyl-3-oxoisoindolin-5-yl)-2-(tert-butoxy)acetate (30 mg, 0.052 mmol) in THF/EtOH (1.5 mL, 2:1) was treated with LiOH (0.5 mL, 2.0 M) and heated to 65° C. After 5 h, the reaction mixture was cooled to ambient temperature and acidified with 1N HCl and extracted with EtOAc. The organics were washed with brine, dried (Na₂SO₄), filtered and concentrated in vacuo. The residue was purified by reverse phase HPLC to afford the title compound (13.4 mg) as a white solid. ¹H NMR (400 MHz, METHANOL-d4) δ=7.42-7.28 (m, 5H), 6.64 (d, J=11.3 Hz, 1H), 5.12 (s, 1H), 4.83 (s, 2H), 4.28-4.23 (m, 4H), 2.90 (s, 3H), 2.74 (t, J=6.5 Hz, 2H), 2.13 (d, J=4.8 Hz, 2H), 1.83 (s, 3H), 1.81 (s, 3H), 1.12 (s, 9H); LC/MS (m/z) ES+=546 (M+1).

The following compounds were prepared in a manner similar to the procedures described above for Examples 1-5.

Example 6: (S)-2-(2-benzyl-6-(4,4-dimethylcyclohex-1-en-1-yl)-4,7-dimethyl-3-oxoisoindolin-5-yl)-2-(tert-butoxy)acetic acid

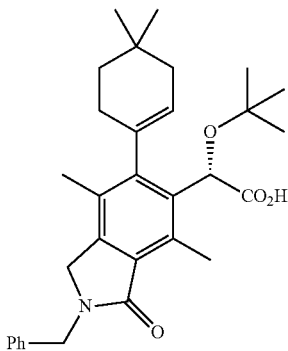 [SMILES: Cc1c2c(c(C)c([C@H](OC(C)(C)C)C(=O)O)c1C1=CCC(C)(C)CC1)C(=O)N(Cc1ccccc1)C2]

The title compound was made in a similar manner as Example 5 except using (4,4-dimethylcyclohex-1-en-1-yl) boronic acid in Step 7. 1H NMR (400 MHz, METHANOL-d4) Shift=7.42-7.24 (m, 5H), 5.73-5.40 (m, 2H), 4.80 (s, 2H), 4.22 (s, 2H), 2.84 (d, J=2.8 Hz, 3H), 2.62-2.49 (m, 1H), 2.18-1.95 (m, 6H), 1.66-1.50 (m, 2H), 1.27-1.18 (m, 9H), 1.16-1.04 (m, 6H); LC/MS (m/z) ES+=490 (M+1).

Example 7: (S)-2-((M)-2-benzyl-6-(8-fluoro-5-methyl-3,4-dihydro-2H-benzo[b][1,4]oxazin-6-yl)-4,7-dimethyl-3-oxoisoindolin-5-yl)-2-(tert-butoxy)acetic acid

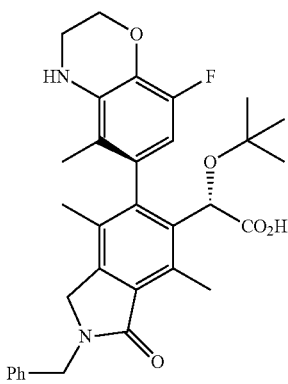

The title compound was made in a similar manner as Example 5 except using 8-fluoro-5-methyl-6-(4,4,5,5-tetramethyl-1,3,2-dioxaborolan-2-yl)-3,4-dihydro-2H-benzo[b][1,4]oxazine (prepared from the known procedure described in WO 2013/12649) in Step 7. 1H NMR (400 MHz, CHLOROFORM-d) δ=7.41-7.28 (m, 5H), 6.27 (d, J=11.0 Hz, 1H), 5.19 (br. s., 1H), 4.90-4.73 (m, 2H), 4.35 (t, J=4.4 Hz, 2H), 4.14 (s, 2H), 3.57 (td, J=4.3, 6.7 Hz, 2H), 2.86 (s, 3H), 1.80 (s, 3H), 1.73 (s, 3H), 1.15 (s, 9H); LC/MS (m/z) ES+=547 (M+1).

Biological Examples

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", Antimicrob. Agents Chemother. 2007, 51: 3147-3154; and Pauwels et al., "Sensitive and rapid assay on MT-4 cells for the detection of antiviral compounds against the AIDS virus", J. of Virological Methods 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). IC50s were determined from a 10 point dose response curve using 3-4-fold serial dilution for each compound, which spans a concentration range >1000 fold.

These values are plotted against the molar compound concentrations using the standard four parameter logistic equation:

$$y=((V\max*x\char`^n)/(K\char`^n+x\char`^n))+Y2$$

where:
Y2=minimum y n=slope factor
Vmax=maximum y x=compound concentration [M]
K=EC50

When tested in the MT4 assay compounds were found to have $IC_{50}$ values listed in Table 1.

TABLE 1

| Example | HIV MT4 Assay $IC_{50}$ (uM) |
| --- | --- |
| 1 | 0.025 |
| 2 | 0.042 |
| 3 | 0.086 |
| 4 | 0.052 |
| 5 | 0.005 |
| 6 | 0.036 |
| 7 | 0.014 |

What is claimed is:
1. A compound of Formula I:

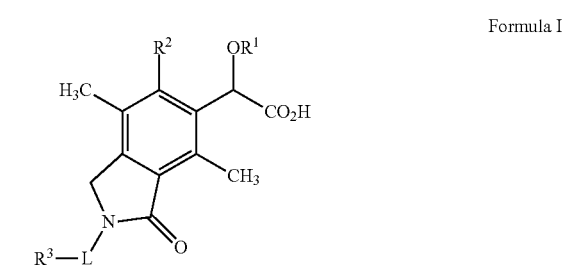

Formula I or a pharmaceutically acceptable salt thereof wherein:

R$^1$ is C$_{1-6}$ alkyl;

R$^2$ is C$_{5-14}$aryl, C$_{3-7}$cycloalkyl, (C$_{3-7}$)cycloalkenyl, (C$_{2-9}$)heterocycle, or (C$_{2-9}$)heteroaryl, each of which is optionally substituted by one to four substituents selected from halo, C$_{1-6}$ alkyl, C$_{1-6}$ hetereoalkyl, or C$_{1-6}$ alkylene or C$_{1-6}$ hetereoalklylene wherein said C$_{1-6}$alkylene or C$_{1-6}$ hetereoalklylene are bonded to adjacent carbon atoms on said C$_{5-14}$ aryl, C$_{3-7}$cycloalkyl, (C$_3$-C$_7$)cycloalkenyl, (C$_2$-C$_9$)heterocycle, or (C$_2$-C$_9$)heteroaryl to form a ring, and wherein each heterocycle, heteroaryl, heteroalkyl, and hetereoalkylene contains one to three heteroatoms selected from S, N or O;

L is a bond or C$_{1-3}$ alkylene: and

R$^3$ is H, C$_{1-6}$ alkyl, C$_{5-14}$aryl, C$_{3-7}$cycloalkyl, (C$_{3-7}$)cycloalkenyl, (C$_{2-9}$)heterocycle, or (C$_{2-9}$)heteroaryl, each of which is optionally substituted by one to four substituents selected from halo, or C$_{1-6}$ alkyl, and wherein each heterocycle and heteroaryl contains one to three heteroatoms selected from S, N or O.

2. The compound or salt according to claim 1 wherein R$^1$ is t-butyl.

3. The compound or salt according to claim 1 wherein R$^2$ is optionally substituted phenyl or optionally substituted cyclohexenyl.

4. The compound or salt according to claim 3 wherein R$^2$ is phenyl optionally substituted by one to four substituents selected from fluorine, methyl, or —CH$_2$CH$_2$CH$_2$O— or —NHCH$_2$CH$_2$O— wherein said —CH$_2$CH$_2$CH$_2$O— or —NHCH$_2$CH$_2$O— is bonded to adjacent carbon atoms on said phenyl to form a bicyclic ring.

5. The compound or salt according to claim 1 wherein R$^3$ is phenyl.

6. The compound or salt according to claim 1 wherein the stereochemistry on the carbon to which OR$^1$ is bound is as depicted below

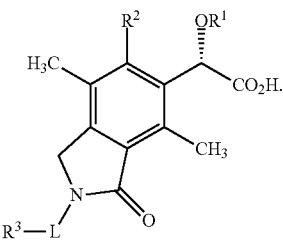

7. A pharmaceutical composition comprising a compound according to claim 1 or a pharmaceutically acceptable salt thereof.

8. A method for treating a viral infection in a patient mediated at least in part by a virus in the retrovirus family of viruses, comprising administering to said patient a composition according to claim 7.

9. The method of claim 8 wherein said viral infection is mediated by HIV virus.

* * * * *